United States Patent [19]
Fugo

[11] Patent Number: 6,079,417
[45] Date of Patent: Jun. 27, 2000

[54] METHOD OF ALTERING THE SHAPE OF THE CORNEA OF THE EYE

[76] Inventor: Richard J. Fugo, 1507 Plymouth Blvd., Norristown, Pa. 19401

[21] Appl. No.: 09/274,902

[22] Filed: Mar. 23, 1999

[51] Int. Cl.[7] .................................................. A61B 19/00
[52] U.S. Cl. ........................... 128/898; 623/4.1; 623/5.11
[58] Field of Search .......................... 623/4, 5, 4.1, 5.11; 128/898; 606/4, 5

[56] References Cited

U.S. PATENT DOCUMENTS

| 550,572 | 4/1895 | Kilmer | 606/1 |
|---|---|---|---|
| 3,945,054 | 3/1976 | Fedorov | 3/13 |
| 4,452,235 | 6/1984 | Reynolds | 128/1 |
| 4,671,276 | 6/1987 | Reynolds | 128/305 |
| 4,766,895 | 8/1988 | Reynolds | 128/303 |
| 4,976,719 | 12/1990 | Siepser | 606/151 |
| 5,300,118 | 4/1994 | Silvestrini | 623/5 |
| 5,413,574 | 5/1995 | Fugo | 606/33 |
| 5,423,815 | 6/1995 | Fugo | 606/50 |
| 5,466,260 | 11/1995 | Silvestrini | 623/505 |
| 5,645,582 | 7/1997 | Silvestrini | 623/5 |
| 5,653,752 | 8/1997 | Silvestrini | 623/5 |

OTHER PUBLICATIONS

Waring III, G. O.. Refractive Keratotomy for myopia and astigmatism. Mosby Yearbook, Inc. pp. 171–257, 1992.

Fugo, R. J.. The Missing Piece to the RK Puzzle: CK. Ophthalmolgy Times, Technique of the Week. Mar. 27—Apr. 2, 1995, p. 48.

Fugo, R. J.. A way to fine–tune vision postoperatively. Ophthalmology Times. Oct. 23–29, 1995. p. 21.

Fugo, R.J.. Compression Keratoplasty: Nonsurgical Enhancement of Radial Keratotomy. Annals of Ophthalmology 1996; 28(3), pp. 140–146.

Smith, Sara. What's Hot in Ophthalmic Development? Ocular Surgery News. Mar. 1, 1998. pp. 30–31.

Sabbagh, Leslie. The Leading Edge: Harnessing electrons for a faster, smarter incision. Eye World, Apr. 1998, pp. 88.

Ruriani, D.C.. Correcting refractive error with radio frequency. Eye World. Nov. 1998. p. 8.

Maddox, R.. Sands of the Sahara Syndrome: Interface inflammation with flap melt following Lasik. Apr. 1, 1998. pp. 41–43.

Brint, S.F.. Lasik technique relies on three steps for perfect cut. Primary Care Optometry News. May 1998. p. 31.

Lipner, M. Sleuthing the SAnds of the Sahara Part II. Eye World. Jan. 1999. pp. 30–31.

Brown, David. Implanting the ICL. Ophthalmology Management. Jun. 1998. pp. 54–55.

Duposar, R.. Hybrid composition of Acrygel lens provides biocompatibility. Ocular Surgery News. oct. 1, 1998 p. 14.

Lipner, M.. Phakic dwellings: Redecorating the ocular interior with vision–boosting designs. Eye World. Nov. 1998. pp. 40–43.

Singer, H.W.. Experimental bo–hinged flap may offer alternative to Lasik. Ophthalmology Times. May 15, 1998. p. 19.

Calderone, J.P.. Eugene Gordon, Medjet defended, Ophthalmology Times Sep. 15, 1998. pp. 4–5.

Mertens, E. LTK Remedies PRK Over–Correction. Euro-Times Cataract and Refractive Times. vol. 2, Issue 1, Feb. 1997, p. 4.

Asiyo–Vogel, M. N.. Histologic analysis of thermal effects of laser thermo–keratoplasty and corneal ablation using Sirius–red polarization microscopy. Journal of Cataract REfractive Surgery vol. 23, May 1997. Abstract.

(List continued on next page.)

*Primary Examiner*—Dinh X. Nguyen

[57] ABSTRACT

A method and device for reshaping cornea 12 wherein radially orientated microintubation channels 32 are surgically created in corneal stroma 30 with surgical microinstrumentation after which corneal shaping devices 34 are inserted into said microintubation channels. Said microintubation channels extend radially from peri-limbal tissue towards the center of said cornea, but not to the very center of said cornea. Said corneal shaping devices place stress on the dome of said cornea and alter corneal topography in a manner that allows for correction of distance vision, near vision, and astigmatism.

16 Claims, 3 Drawing Sheets

OTHER PUBLICATIONS

Sanders, Donald, R. LTK analysis pinpoints optimum parameters. Ocular Surgery News. vol. 15, No. 19, Oct. 1, 1997. p. 50.

Moretti, Michael. Ophthalmologists invest in LTK future. Eye World. Feb. 1999. p. 14.

Neumann, A.C. Hyperopic thermokeratoplasty: Clinical Evalustion. J. Cataract Refractive Surgery, vol. 17, Nov. 1991. p. 830.

Charpentier, D.Y.. Hot Needle Thermal Keratoplasty to Correct Naturally Occuring Hyperopic Astigmatism. J. Refractive Surgery vol. 12, Sep./Oct. 1996, p. 705.

BiSantis, C.. Intrastromal perioptic implants correct myopia but avoid visual axis. Ocular Surgery News. vol. 15, No. 19, Oct. 1, 1997, p. 48.

Uhl, J.G.. ICRS offers advantages for treating low to moderate myopia. Primary Care Optomerty News. vol.3, No. 5, May 1998, p. 30.

Fundingsland, B. The Adjustable Corneal Ring. Eye World, Jan. 1999. p. 32.

Smith, S.E. Keravision Intacs recommended for FDA approval. Ocular Surgery News, vol. 17, No. 4, Feb. 15, 1999. pp. 19–21.

Fink, A.M. Corneal Changes Associated with Intrastromal Corneal Ring Segments. Arch. Ophthalmology, vol. 117, Feb. 1999. p. 282.-

METHOD OF ALTERING THE SHAPE OF THE CORNEA OF THE EYE

BACKGROUND FIELD OF INVESTIGATION

This invention relates to an apparatus and method for providing changes in the shape and topography of the cornea of the eye globe, specifically a new method and prosthetic device which may be inserted into corneal tissue thereby providing a method to change the shape and topography of the cornea.

BACKGROUND DESCRIPTION OF PRIOR ART

Physicians during the 1800s made significant attempts at changing the topography of the cornea in an effort to alter the curvature of the cornea thereby producing a desired change in the eye wear needs of patients. A resurgence in interest in changing the corneal topography occurred before the Second World War under the guidance of Professor Tsutomu Sato of Juntendo University, Tokyo. The problems with Dr. Sato's experimentation and research mainly revolved around the complications and damage to the inner or endothelial cell layer of the cornea. The endothelial cells of the cornea are the inner most layer of the cornea and are one cell layer thick. These cells largely are non-replicating thereby damage to them results in an irreversible harm to cornea. Dr. Sato had many approaches including placing a thin sharp knife into the tissue of the eyeball which is known as sclera outside of the ring around the clear cornea known as the limbus of the eye. This thin sharp knife was then moved towards the center of the cornea in the central portion of the corneal body before it was then turned towards the inner portion of the cornea and the blade was then used to make perforating incisions into the inner half of the corneal structure. This incision into the inner half of the cornea damaged endothelial cells which came in contact with the incising blade. This largely produced an irreversible damage to the endothelial cells which themselves serve to pump water out of the central portion of the cornea which is known as the corneal stroma. If this water is allowed to accumulate in the stroma, the cornea becomes hazed or clouded and eventually takes on a whitish opaque appearance, wherein the appearance of the cornea is substantially like that of the white scleral tissue which surrounds the normally clear cornea. Dr. Sato actually attempted numerous approaches to control the curvature or topography of the cornea of the eye. This brought on the widely held belief that incising cornea tissue in order to alter the shape of the cornea with the purpose of reducing dependence upon eye wear was inevitably damaging normal corneal tissue and thereby unethical. Nonetheless in the 1960s, Dr. Svyatoslav Fyodorov, MD of the former Soviet Union again championed the cause for placing incisions in a specific pattern into the cornea in order to produce wanted change in corneal topography in order to decrease dependency or need for eyeglasses or other eye wear. Dr. Fyodorov's reported statistics were highly scrutinized in the United States of America by American ophthalmologists who for the large part remained adamant that this procedure was unethical because it incised and damaged normal corneal tissue. Nonetheless, Dr. Fyodorov produced an "assembly line" surgical suite in which multiple surgeons and technicians performed these surgeries on patients. In retrospect, Dr. Fyodorov's work was indeed pioneering although still today some of the data reported in his earlier works remains suspect in ophthalmic circles.

In 1976, the American eye surgeon Dr. Leo Bores traveled from the United States to Moscow in order to observe intraocular surgery performed by Dr. Fyodorov. During this visit, Dr. Bores not only witnessed intraocular surgery with intraocular implants but also observed the Russian procedure to place radial incisions in the front of the cornea which has come to be known as Radial Keratotomy. The procedure was performed to minimize the optical condition of myopia or nearsightedness. The theory upon which this procedure is based is substantially that when appropriate incisions are made in the mid and peripheral portions of the cornea and placed in a radial fashion that these incisions in fact cause a controlled ectasia or bulging of the cornea in the mid-peripheral zone, thereby indirectly producing a flattening of the central portion of the cornea. In effect, this converts the cornea from a more hill-like topography to a more plateau-like topography. Dr. Richard Fugo and coworkers established that radial keratotomy reduced myopia by adding tissue to the circumference of the cornea. Fugo termed this corneal tissue a "corneal microwedge" and based on this finding created a new, safer method of refining the visual outcome of radial keratotomy through a technique called "Compression Keratoplasty", which allowed surgeons to avoid the risk of additional incision into corneal tissue.

Much resistance to Radial Keratotomy was encountered by Dr. Bores when he returned to the United States and attempted to disseminate the information which he had been taught by Dr. Fyodorov in the Soviet Union. Nonetheless, the views perceived early on by ophthalmologists on the procedure known as Radial Keratotomy soon gave way to a new appreciation and understanding of this procedure. This procedure was eventually so well received in the ophthalmic community that it became one of the most written about and talked about procedures in ophthalmology outside of cataract surgery in the latter part of the 1980s and the early portion of the 1990s. This trend occurred in the arena wherein conservative establishment ophthalmologists severely attacked more adventuresome ophthalmic surgeons.

However, technology caught up to the reign of Radial Keratotomy in ophthalmology as Eximer Laser technology improved. The early 1980s brought on a germinal interest in "Laser Corneal Surgery". This surgery was based on the utilization of the Eximer laser. The Eximer laser was placed through rigorous international as well as United States Food and Drug Administration protocols. During the 1990s, the Eximer laser has won progressively more governmental approvals internationally as well as in the United States of America for human corneal use. Unlike the standard Radial Keratotomy, the Eximer laser utilized a laser beam to reshape the center portion of the cornea. This is probably the most precarious aspect of Eximer Laser. That is to say, Eximer laser ablates or causes microscopic surface incisions into the center of the cornea. The central portion of the cornea is the most important part of the cornea with regards to vision. Therefore, we are cutting, albeit with laser, the portion of the cornea that is most critical for vision whereby if damage to this section occurs from any means such as scar formation then vision is damaged. On the other hand, Radial Keratotomy's strongest argument is that it does not cut the very center of the cornea and thereby allows the most critical corneal tissue for vision to remain virgin. Nontheless, even the midperipheral incisions into the cornea with Radial Keratotomy may produce debilitating glare and irregularities in the corneal surface known as irregular astigmatism which itself can be vision threatening.

The biggest problem with both Radial Keratotomy and Eximer Laser is that they are irreversible. Once these operations are performed, one may re-operate or as it has been promoted with a positive sounding term called "surgical enhancement". Surgeons may attempt to surgically improve the vision of the patient with a second or third or fourth operation which they tell the patient is an "enhancement procedure". However, the accuracy of vision correction becomes less with each repeat surgery. Another major problem with Eximer laser is that it removes the layer immediately beneath the top surface of the cornea, namely it removes Bowman's membrane. Recall that the cornea has 5 layers beginning from the outside of the eye: the epithelial layer, Bowman's membrane, stroma, Descemet's membrane, and endothelium. For many years, it was believed that removal or damage to Bowman's membrane would produce irrevocable long term chronic corneal disease. This was a widely held belief of ophthalmologists because when a cornea trauma occurred and the Bowman's membrane was violated, it was found that that portion of the cornea often experienced repeated chronic disease processes such as recurrent corneal erosions. However, the proponents of the Eximer laser claim that Bowman's membrane is truly a "gallbladder of the eye" wherein it is a structure not needed by the cornea. This argument is far from conclusive and largely unsolved. No one knows what the long term effect of removal of the Bowman's membrane by the Eximer laser will have on the cornea since the temporal longevity of the Eximer experience to date is relatively short.

Numerous other techniques have been proposed to eliminate eyeglasses such as implantable contact lenses. In this procedure, an incision is made into the eye such is made in the procedure for cataract surgery. In this case, an implantable lens is placed into the eye. Intraocular surgeries bring with them significant risks of infection and thereby endopthalmitis as well as other problems such as irritation of the uveal tissue with concomitant chronic iritis. To date, this procedure is not widely utilized throughout the world. Other modalities to alter corneal topography include holmium thermal keratoplasty wherein a holium laser is utilized to employ heating discrete spots in precise corneal locations in order to contract the corneal collagen fibers and thereby change the shape of the cornea. Grave problems have included unpredictability of final outcome with unpredictable drift and shifting of the corneal topography with time. Also, significant scar formation on an aesthetic visible level is notable. A similar technique is employed wherein a radiofrequency electronic system is utilized to place heat into the corneal stroma utilizing needles which are connected into an electronic system that generates a heat in the needle. Cruder attempts included placing a hot regular needle into the corneal structure in order to shrink and contract the corneal stroma in order to change the corneal topography; however, this procedure is not well tolerated. Radio frequency energy has been employed to reshape the cornea. Bipolar diathermy has also been employed to reshape the cornea.

Intrastromal corneal rings have been utilized to attempt to alter the topography and shape of the cornea. With this procedure, rings of translucent material such as a PMMA (Polymethylmethacrylate) plastic are inserted into the mid-peripheral portion of the stroma of the cornea. In order to place a round ring of material into the body of the cornea, specific dissector equipment is utilized in order to make a tunnel from the outside of the cornea through the epithelial layer of the cornea and into the stroma of the cornea. Once the stroma is reached, the dissector equipment is used to dig a channel or cut channels or create channels in a ringed fashion around the center axis of the cornea thereby attempting to stay in the mid-peripheral portion of the cornea. The problem with this procedure is quite simply that the incision begins in cornea quite close to the very center of the cornea, namely the tissue that is critical for vision in the eye, as previously discussed in this section. Other concerns include irregular thicknesses in the cornea wherein the blade cuts the circular path around the center of the cornea through the corneal stroma causing penetration into the inner chamber of the eye thereby producing the possibility of an infectious contamination of the inside of the eye with a subsequent endophthalmitis. Since the path substantially encircles the pupil while attempting to remain in the stroma of the cornea, accidental stress on the cutting device could in effect rip or tear up large sections of the mid-peripheral portion of the cornea and potentially the central portion of cornea tissue. Emphasis must be placed on the fact that the intrastromal ring encircles and thereby traumatizes substantial amounts of cornea very close to the light focusing, central visual axis of the cornea. Intrastromal corneal rings perforate the corneal epithelium in the mid-peripheral cornea, creates a corneal tunnel in mid-peripheral cornea and places circular prostheses around the pupil in mid-peripheral corneal tissue. The degree and extent of mid-peripheral trauma results in extensive damage to corneal nerves which run in a direction substantially perpendicular to the path of the Intrastromal Corneal Ring. Additionally, all of the corneal stroma tunnel formation and implantation of the prosthetic material of the intrastromal corneal ring occur within tissue immediately adjacent to the center of the cornea. This degree of trauma to the corneal tissue adjacent to the center of the cornea has resulted in significant damage to the endothelial cells of the cornea in a significant number of patients. This endothelial cell damage was identified and quantitated by the United States Food and Drug Administration (FDA) Ophthalmic Devices Panel and was reported in Ocular Surgery News, Vol. 17, #4, pgs.19–21, Feb. 15, 1999. Furthermore, the intrastromal corneal rings form a circular pattern thereby substantially remaining parallel to the pupil margin and the limbus of the eye. Therefore, the body of the intrastromal corneal ring creates a round bulge on the outer surface of the cornea with concomitant round grooves or furrows running along side of the round corneal bulge. These round furrows create a round stagnation trough where tears collect with subsequent precipitation of iron atoms out of the tear film with collection and deposition into the corneal tissue. The resultant circular iron lines in the cornea are found adjacent to intrastromal corneal rings and have been confirmed by several authors.

Methods employed in other areas of technology wherein high-pressure water streams are used to incise materials including steel have been transferred into the field of ophthalmology. Companies are actively employing water jets to place incisions into corneal tissue in an attempt to create changes in corneal topography as well as to create a bisection or flap of the center portion of the cornea which is known as a corneal flap. This technique has classically been produced using a device known as a keratome which substantially employs a circular vacuum device which sucks a cutting head onto the surface of the eye and then allows a surgeon to activate the movement of a sharp razor type blade across the eye which is sufficiently close to the eye such that it will actually cut a flap of cornea on the front surface of the eye. This procedure creates a flap of corneal tissue through the stroma of the eye with the epithelial side on one half of the flap and the endothelial surface on the other side of the corneal flap. This procedure has recently become quite popular in the procedure known as "LASIX" or "Flap and Zap". In this procedure, an ophthalmic surgeon uses a keratome to make a bisection of the front surface of the eye and then employs the Eximer laser which has been discussed previously to remove corneal tissue from the central portion of the corneal flap upon which the endothelial cells lie. By Eximer lasing of the stromal base, one is able to remove stromal tissue thereby alter the total topography of the cornea. This was initially touted as the ultimate keratorefractive procedure. However, experience has taught us that severe consequences may occur with this procedure. For example, it is not unusual for surgeons to report that the flap has been destroyed because of a malfunction of the keratome. It is not unusual for surgeons to accidentally loose the top portion of the flap secondary to surgeon error or equipment error. This is devastating to the visual outcome of the patient. Now more reports are being published which demonstrate that infectious as well as noninfectious inflammations along with severe haze are occurring along the flap interface when the flap is replaced at the end of the Eximer laser procedure. Some have insinuated that various oils and solutions used to maintain the keratomes may be leaking into the flap bed interface thereby creating a chemical inflammation of that interface along with a clouding of the cornea. Others have raised the issue of the complete and total excision of corneal nerves as the guillotine style incision by the razor blade type mechanism cuts through cornea. Our invention employs radially orientated channels called microintubation channels created in the stroma of the cornea. Into the radial intubation channels, we insert a prosthestic device called a corneal shaping device or a corneal contouring device or a corneal stent. Although it has been thought that a radially orientated corneal prosthesis is not feasible to alter corneal topography, the discovery of the concept of corneal microwedges and other findings in cornea dynamics by the inventor caused the inventor to rethink and challenge this point of view. As it turns out, corneal stents are actually superior to the other cited approaches to alter corneal topography and also to eliminate many of the side effects of the other approaches.

OBJECTS AND ADVANTAGES

Several objects and advantages of the present invention are:

(a) to provide a corneal contouring device known as a corneal stent which may be placed into a microintubation channel in the stroma of the cornea by an entry channel which is created in the white sclera of the eye or even the limbal tissue or substantially close to the limbal tissue of the eye.

(b) to provide a corneal contouring device which may be inserted into the cornea in a radial or substantially radial fashion in order that each such radial stent will contact minimal corneal tissue in the mid-peripheral zone of the cornea and contact no corneal tissue in the absolute central portion of the cornea.

(c) to provide a corneal stent which provides a reduced possibility of trauma to the corneal structure as opposed to present day technology.

(d) to provide a corneal stent which contains a specific rigidity and/or radius of curvature to alter corneal topography.

(e) to provide a corneal stent which provides a reduced incidence of trauma to corneal tissue.

(f) to provide a corneal stent which produces a substantially reduced risk of creating iron deposit lines around the stent.

(g) to provide a corneal stent which possesses a minimal potential to inadvertently rip or tear any corneal tissue.

(h) to provide a corneal stent which is relatively easily removed and/or replaced by a trained ophthalmic surgeon.

(i) to provide a corneal stent which may create a less painful and better tolerated change in topography or surface shape of the cornea.

(j) to provide a corneal stent which provides a reversible change in corneal topography or shape.

(k) to provide a method of reversibly altering the corneal topography or corneal shape thereby altering the total optical characteristics of the eye.

(l) to provide a method of reversibly altering the eye glass or eye wear needs of the patient thereby minimizing the dependence for eyeglasses.

(m) to provide a method of altering the topography or shape of the cornea in which radial prostheses placed into the cornea are individualized such that they may independently alter the change in topography or shape in a given quadrant of the cornea.

(n) to provide a flexible method to change corneal topography in different quadrants or section of the cornea thereby allowing neutralization of astigmatism and reversal of presbyopia.

(o) to provide a method of reducing the need for reading glasses by specifically altering given corneal stents to modify the curvature of the inferior cornea such that it will neutralize the need for reading glasses and presbyopia.

(p) to provide a method of being able to periodically adjust the corneal topography based on changes in the refractive system in other parts of the eye such as an early cataractous myopic shift or age related shift in corneal astigmatism.

(q) to provide a method wherein eye surgeons can substantially refine visual needs throughout life based on shifts in the ocular status with age or disease processes.

(r) to provide a means of returning the patient to their original refractive error should the patient so decide that that was a more desirable visual status for that given patient.

(s) to provide a means of correcting a refractive error without violating virgin central cornea with minimal prosthesis or stent surface contact with mid-peripheral corneal tissue.

(t) to provide a means of correction of refractive error with minimal visual distress to the patient such as halos, glare or visual distortion.

DRAWING FIGURES

These figure drawings are enclosed which show portions of the eye with special attention to details of the cornea of the eye.

REFERENCE NUMERALS IN DRAWINGS

10 Sclera
12 Cornea

Figure 3:
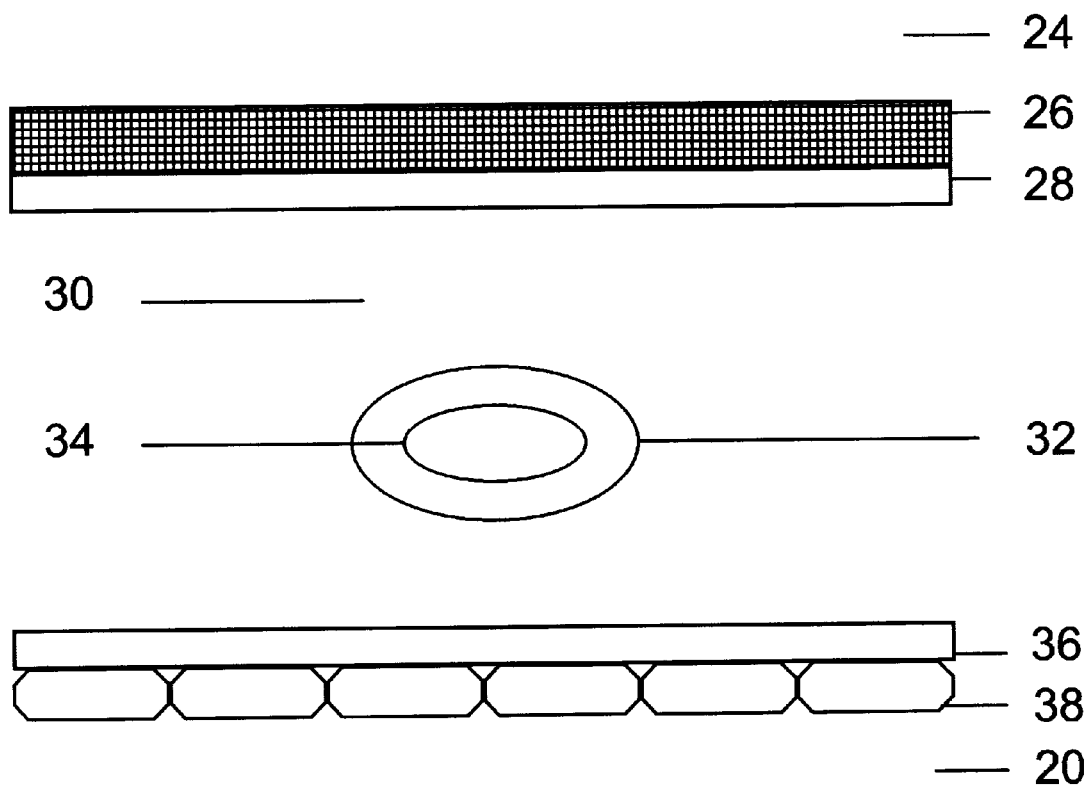
FIG. 3 shows a cross section view of cornea as shown in reference numeral 40 in FIG. 2, wherein a cross section view of a microintubation channel and corneal shaping device are displayed in a relative fashion for dimensions are not drawn to scale.

14 Limbus
16 Iris
18 Pupil
20 Anterior chamber
22 Eye lens
24 Exterior of eye
26 Epithelium
28 Bowman's membrane
30 Stroma
32 Microintubation channel
34 Corneal shaping device
36 Descemet's membrane
38 Endothelium or Endothelial Cells
40 Plane of Cornea Section displayed in FIG. 3
42 Perforation site to initiate microintubation channels

SUMMARY

Accordingly, it is one object of the present invention to provide in a corneal shaping device and improved method of contouring the topography of the cornea.

It is another object of the present invention to provide a corneal contouring device which minimizes the risk of damaging or traumatizing the tissue of the cornea thereby providing a method of minimizing dependence on eye wear while minimizing the risk of surgical complications.

It is still another object of the present invention to provide a corneal shaping device which will allow reversible replacement of corneal stents thereby providing a method of reversible vision correction.

It is yet another object of the present invention to provide a corneal shaping device which requires minimal incision or cutting of the central corneal tissue thereby providing a method of reversing the need for eyewear while minimizing the risk of structural damage to the central cornea which is the critical portion of the cornea for refraction of light for vision.

It is yet another object of the present invention to provide a corneal shaping device which requires substantially less cost for equipment as well as the operative procedure in order to correct the refractive errors and thereby reduce the dependence on eyewear as opposed to presently available refractive procedures for the eye.

It is yet another object of the present invention to provide a corneal shaping device which will allow a method whereby the shape of different quadrants may be altered independently by using different properties or types of corneal stents thereby allowing for the correction of undesirable corneal shapes such as astigmatism.

It is a further object of the present invention to provide a corneal shaping device which allows the inferior cornea to be shaped differently than the superior portion of the cornea thereby allowing a surgeon to adjust distance vision as well as near vision and thereby minimize the need for distance glasses as well as reading glasses for presbyopia.

It is a further object of the present invention to provide a corneal shaping device which may be easily removed from the cornea thereby providing a method of returning the refractive error of the eye to its original state.

It is yet a further object of the present invention to provide a corneal shaping device which may be easily replaced or exchanged with alternate corneal stents thereby providing a method of efficiently refining the corneal topography as required by patient need or changes in the optical system of the eye such as may be induced by disease or cataract lens changes with impact on the overall optical refractive power of the eye.

Figure 1:
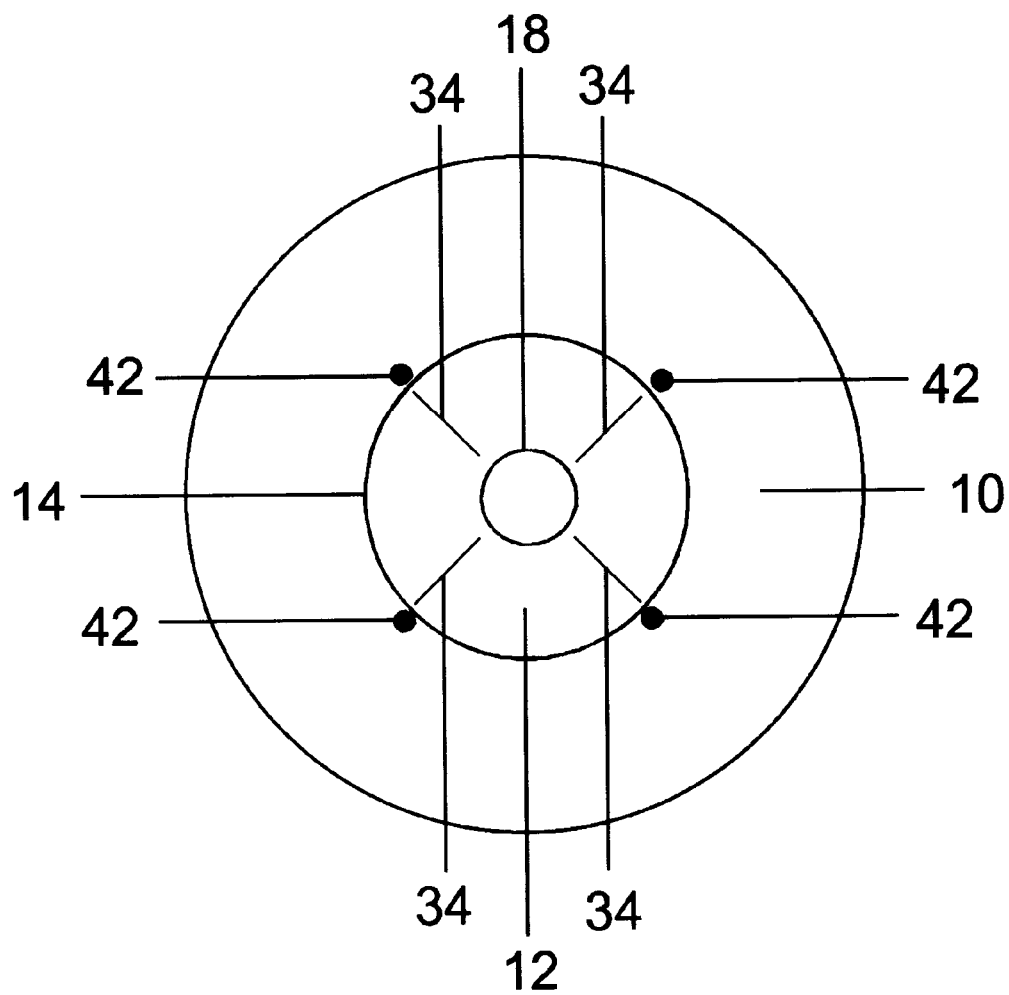
FIG. 1 shows a front view of the eyeball with all other surrounding tissue such as eyelids and orbital structures eliminated.
Figure 2:
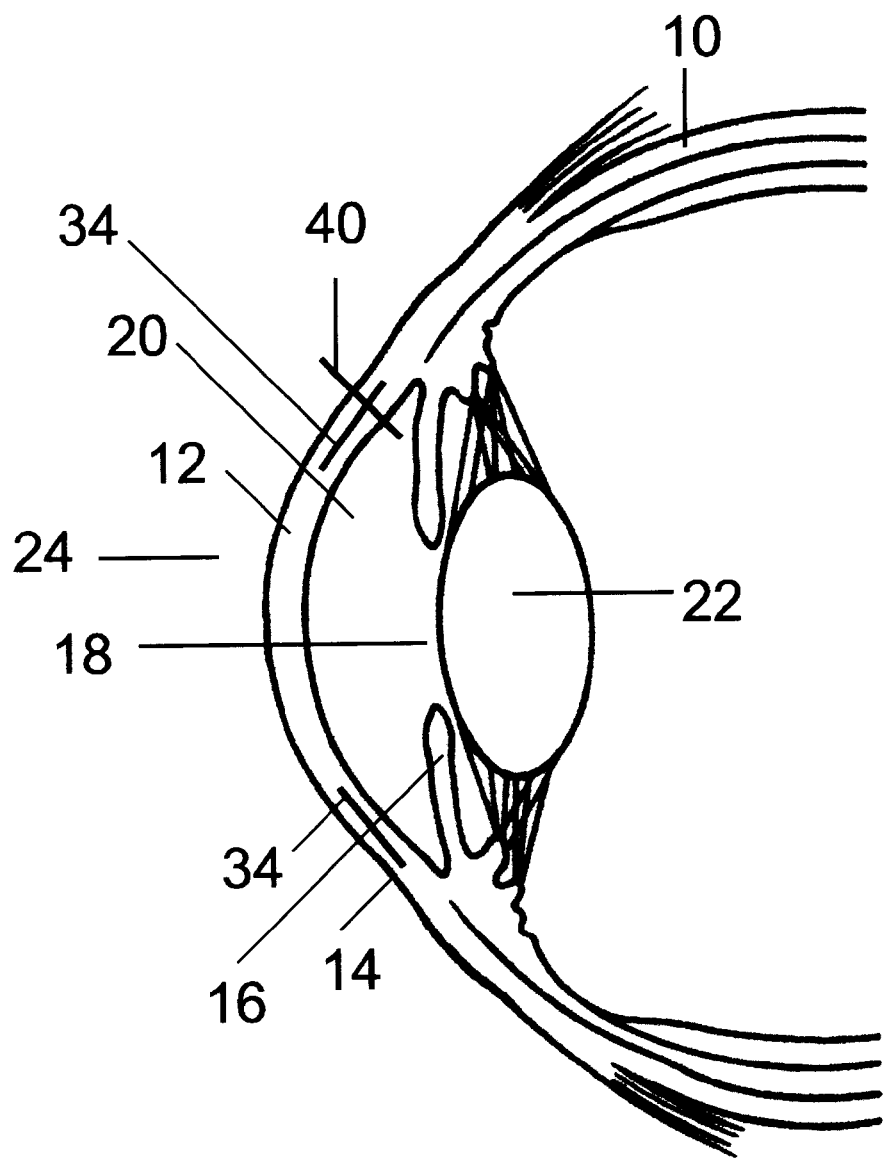
FIG. 2 shows a sagittal plane section through the center of the front portion of the eyeball.

Description—FIGS. 1 to 3

A typical embodiment of a corneal shaping device 34 of the present, invention is illustrated in FIG. 1 to FIG. 3. The anatomy of an eye has specific features. FIG. 1 demonstrates a front view of an eye. FIG. 2 demonstrates a sagittal section plane through a center of the front portion of an eye. FIG. 3 demonstrates a section through mid-peripheral cornea 40. A perforation site 42 to initiate microintubation channels 32 is placed in white sclera 10 or tissue substantially near limbus 14. Sharp ophthalmic micro-instrumentation is employed to create a perforation site 42 to initiate microintubation channels 32. The sharp ophthalmic micro-instruments then tunnel towards the center of the pupil in a radial fashion through sclera 10, limbus 14 and cornea 12. Microintubation channels 32 are substantially radial in orientation to cornea 12. A microintubation channel 32 penetrates towards the center of cornea 12 however does not enter into central corneal tissue over a constricted pupil 18. A microintubation channel 32 is created with micro-surgical ophthalmic instrumentation which is constructed to generate tunneling through stroma 30 of cornea 12 and avoiding perforation of Decement's membrane 36 and endothelial cells 38, thereby avoiding penetration into an anterior chamber 20 of an eye. Corneal shaping devices 34 also known as corneal stents or corneal prosthesis are inserted into microintubation channels 32 that are created within cornea 12 of an eye. Corneal shaping devices 34 enter corneal tissue through perforation sites 42 located in sclera 10 or tissue substantially close to limbus 14.

Operation—FIGS. 1 to 3

The manner of using a corneal shaping device 34 in cornea 12 of an eye employs a device and method which allows insertion of a device which will change the topography or shape of the cornea while minimally damaging corneal tissue. One of the problems with intrastromal rings presently employed in ophthalmology is a notable trauma or damage to corneal nerves mainly because an incision path to implant an intrastromal ring is circular in formation and is centered around pupil 18. Since corneal nerves run substantially radial to corneal tissue, a circular incision as seen in the case of intrastromal corneal rings will by necessity have a high probability of intersecting corneal nerves because the incision path is perpendicular to nerve. This process also creates circular furrows in cornea adjacent to the intrastromal corneal ring with subsequent iron deposits in the corneal furrow. The substantial radial course of a corneal shaping device 34 substantially reduces these risks. The cross-sectional shape whether oval, triangular or circular or otherwise of a corneal shaping device 34 also known as a corneal stent or corneal contouring device is nonspecific. The integrity of a corneal shaping device 34 is based on any material with significant rigidity and tissue compatibility such that the corneal stent will cause a stress on the cornea and thereby create a change in the shape or topography of the cornea. A corneal shaping device 34 is inserted into a microintubation channel 32 which was previously created. In order to form a microintubation channel 32, a sharp pointed microsurgical instrument is used to create a perforation site 42 into white sclera 10 or tissue substantially near limbus 14. Once the micro-instrumentation penetrates into the sclera/limbus/cornea, the instrument is progressively inserted in a radial fashion such that it creates a microintubation channel 32 in the body of stroma 30 of cornea 12. The micro-instrumentation device is orientated in a stromal plane and avoids violating Descemet's membrane 36 or endothelial cells 38 and thereby fails to penetrate into anterior chamber 20 of an eye. The microintubation channel remains in a substantially radial path with regards to the circumference of cornea 12. The microintubation channel also stops before approaching central corneal tissue over constricted pupil 18. Following creation of the microintubation channel, the ophthalmic microintubation incising channel-creating device is withdrawn from the microintubation channel and the process of microintubation channel creation is repeated as needed by the ophthalmic surgeon. Once a microintubation channel 32 is created, an appropriate corneal shaping device 34 is then inserted into the radially orientated microintubation channel 32. The particular corneal shaping device is chosen based on specific length, rigidity characteristics, and material characteristics in order to place specific stress and tension on corneal tissue. A corneal shaping device 34 creates a mechanical stress effect when inside of a corneal microintubation channel 32 and thereby creates a change in the shape or topography of the cornea. The specific cross-sectional geometry of a corneal shaping device 34 is nonspecific and may be oval, round, star shaped, or otherwise. The material used in the construction of a corneal shaping device 34 is specific only to the extent that it need possess mechanical characteristics and strength to change the shape of the cornea and specific to the extent that the material is tolerated by corneal tissue rather than induce a substantial inflammatory reaction or a rejection reaction by corneal tissue. The number of microintubation channels 32 and thereby the number of corneal shaping devices 34 in a given cornea 12 depends on the surgeon's surgical design for keratorefractive surgery. Corneal shaping devices 34 may be individualized in order to correct irregularities in the cornea such as corneal astigmatism. Corneal shaping devices 34 may also be individualized in order to change the topography of the inferior portion of cornea 12 as opposed to the superior portion of cornea 12 in order to correct distance vision as well as near vision in patients who suffer from presbyopia. Once corneal shaping devices 34 are in place, the surgeon will utilize individual post-operative choices that best protect the patient such as the use of topical antibiotics and topical steroids or systemic antibiotics and systemic steroids. Post-operative pain medication is individualized for patients' safety according to good medical judgment. If during the insertion or after the insertion, a given corneal shaping device is fractured or damaged, then only that one corneal shaping device 34 will need to be withdrawn through an original perforation site 42 and replaced with an undamaged corneal shaping device 34. The patient will then have the opportunity to subjectively evaluate the acceptability of the change of vision created by insertion of a cornea shaping device 34 in a given eye. If the patient is not satisfied, then the vision may be refined by removing individual corneal shaping devices 34 or all corneal shaping devices 34 through a perforation site 42 without needing to place an incision into corneal tissue. Vision may then be refined by inserting corneal shaping devices 34 with different physical characteristics to alter corneal topography in a way that will improve or refine vision. This process may be repeated for one corneal shaping device 34 or multiple corneal shaping devices 34. The decision will be based on patient subjective evaluation of vision as well as sound medical judgment. In the event that a patient decides that their original vision was subjectively more desirable than the new adjusted vision, then corneal shaping devices 34 may be removed from microintubation channels 32 and the shape of the cornea will return to its preoperative topography or shape. In this way., the patient's vision will be returned to their original preoperative vision.

Conclusions, Ramifications and Scope

Accordingly, the reader will see that the corneal shaping device of this invention may easily, safely, and conveniently be inserted, exchanged, or removed by an experienced ophthalmic surgeon. Furthermore, our invention has the additional advantages in that It permits the insertion of corneal contouring devices called corneal shaping devices, corneal stents or corneal prosthesis which have no need to surgically cut or incise the central cornea thereby maximizing the preservation of this critical section of cornea for vision;

It permits the insertion of intrastromal corneal stents which have a much reduced chance of laceration or tearing of corneal stromal tissue than presently utilized refractive systems;

It provides a technique of improving the refractive system of the eye which is completely reversible and which may be more easily refined than presently employed refractive surgical techniques;

It employs a surgical refractive technique which completely preserves the Bowman's membrane of the cornea which is violated substantially with Eximer laser surgery, less substantially with Radial Keratotomy and somewhat violated by intrastromal corneal rings;

It provides a corneal shaping device which avoids entering the anterior chamber of the eye and thereby greatly reduces the risk of an infection in the eye such as endopthalmitis;

It provides a corneal shaping device that substantially reduces the risk of ripping or significantly tearing mid-peripheral tissue over presently employed techniques such as intrastromal corneal rings;

It provides a corneal shaping device which substantially reduces the amount of trauma to central corneal tissue over presently employed systems such as Eximer laser and intrastromal corneal rings;

It provides a corneal shaping device which substantially reduces the risk of perforation and entry into the anterior chamber of the eye over currently employed keratorefractive techniques such as LASIX, Eximer laser surgery, radial keratotomy and intrastiromal corneal rings;

It provides a corneal shaping device which dramatically reduces the cost of equipment needed to perform keratorefractive surgery thereby providing a cost effective technique to correct refractive errors and reduce the dependence of eye wear compared to presently available keratorefractive surgeries;

It provides a corneal shaping device that provides a method of changing the shape of different quadrants of the cornea to a different level or different degree thereby providing a method to correct irregularities in the cornea such as astigmatism;

It provides a corneal shaping device which allows a method of altering the contour topography of the superior cornea differently than the contour topography of the inferior cornea thereby allowing a method to address the problem of distance vision concomitantly with near vision therein eliminating the need for glasses for both distance vision as well as near vision; and It provides a corneal shaping device that allows a method of improving vision while reducing the risk of surgical complication wherein damage to an individual corneal stent would require replacement of only the damaged corneal stent.

Although the description above contains much specificity, these should not be construed as limiting the scope of the invention but as merely providing illustrations of some of the presently preferred embodiments of this invention. For example, the corneal shaping device can have many cross-sectional geometric shapes such as circular, oval, trapezoidal, triangular, etc.

Thus the scope of the invention should be determine by the appended claims and their legal equivalents, rather than by the examples given.

I claim:

1. A method for placing corneal shaping devices also known as corneal contouring devices or corneal stents into microintubation channels located in stroma of cornea of an eye said method comprises creating said microintubation channels and placing said device into said microintubation channels wherein said microintubation channels are oriented substantially perpendicular to limbus and to pupil of said eye.

2. The method of claim 1 wherein said corneal shaping devices are constructed of ridged or semi-ridged material thereby allowing said corneal shaping device to generate a stress on said cornea whereby a change in corneal shape or corneal topography is produced.

3. The method of claim 2 wherein said corneal shaping devices are non-specific with regards to cross-sectional geometry whereas said corneal shaping devices are substantially linear or curvilinear along a geometric long axis, even possessing angles in said material along said geometric long axis.

4. The method of claim 1 wherein said microintubation channels are created by a sharp ophthalmic micro-surgical instrument which is used to create an outer surface penetration site of eye sclera or peri-limbal eye tissue then tunnels through said stromal tissue of said cornea with a substantially radial orientation with reference to said limbus.

5. The method of claim 4 wherein said corneal shaping devices may be inserted into said microintubation channels in said corneal stroma by progressively feeding said corneal shaping device through said penetration site in said outer surface of said eye sclera or said perilimbal eye tissue until said corneal shaping device is seated in said microintubation channel without the need to surgically cut or incise central corneal tissue thereby maximizing preservation of a most critical portion of said cornea for focusing of an image and good vision.

6. The method of claim 1 wherein insertion of said corneal shaping devices may be performed with a much reduced potential for laceration or tearing of said corneal stromal tissue as opposed to presently utilized refractive surgical systems.

7. The method of claim 1 wherein said corneal shaping devices are inserted into said microintubation channels of said cornea stroma in a manner which preserves Bowman's membrane of said cornea thereby preserving histologic integrity and viability of said cornea.

8. The method of claim 1 wherein said insertion of said corneal shaping device allows a reduced risk of inadvertently penetrating into anterior chamber of said eye, thereby greatly reducing said risk of secondary intraocular infection.

9. The method of claim 1 wherein said insertion of said corneal shaping device substantially reduces said risk of traumatizing and damaging mid-peripheral corneal tissue as compared to presently employed techniques for intracorneal prostheses.

10. The method of claim 1 wherein said insertion of said corneal shaping device reduces a substantial amount of trauma to central and said mid-peripheral corneal tissue over presently employed systems of refractive surgery such as eximer laser and intrastromal corneal rings, whereby our keratorefractive system provides improved said vision with less said risk or potential complications.

11. The method of claim 1 wherein said insertion of said corneal shaping device will provide greatly reduced cost for equipment needed to perform said refractive surgery thereby providing a technique to correct refractive errors and reduce dependence on eyewear in a more cost effective fashion over presently available keratorefractive surgeries.

12. The method of claim 1 wherein said insertion of said corneal shaping device provides said method of independently changing said corneal shape of different quadrants of said cornea to different degrees or magnitudes thereby providing said method to correct irregularities in said corneal topography such as astigmatism.

13. The method of claim 12 wherein said insertion of said corneal shaping device provides said method of altering said corneal shape and said corneal topography of a superior portion of said cornea substantially independent of changing said corneal shape and said corneal topography of an inferior portion of said cornea thereby allowing said method to correct distance vision concomitantly with near vision therein reducing or eliminating a need for eyeglasses or said eyewear for both said distance vision as well as for said near vision.

14. The method of claim 1 wherein said insertion of said corneal shaping devices allows for reducing said refractive errors of said eye in said manner which is reversible and which allows said vision to be refined by a surgeon by surgically exchanging individual or multiple said corneal shaping devices.

15. The method of claim 1 wherein said corneal shaping device allows for said method for improving said vision with said reduced risk of said potential complications wherein damage to individual said corneal shaping devices would require surgical removal of individual said corneal shaping devices without needing to remove undamaged said corneal shaping devices from a remainder of said corneal tissue.

16. The method of claim 1 wherein said corneal shaping device minimally damages corneal nerves, corneal epithelium and corneal endothelial cells thereby said corneal shaping device produces minimal decrease in corneal sensitivity and translucency.

* * * * *